(12) United States Patent
Nakamura et al.

(10) Patent No.: US 9,562,944 B2
(45) Date of Patent: Feb. 7, 2017

(54) SEMICONDUCTOR DEVICE INSPECTION DEVICE AND SEMICONDUCTOR DEVICE INSPECTION METHOD

(71) Applicant: HAMAMATSU PHOTONICS K.K., Hamamatsu-shi, Shizuoka (JP)

(72) Inventors: Tomonori Nakamura, Hamamatsu (JP); Mitsunori Nishizawa, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/764,246

(22) PCT Filed: Jan. 30, 2014

(86) PCT No.: PCT/JP2014/052146
§ 371 (c)(1),
(2) Date: Jul. 29, 2015

(87) PCT Pub. No.: WO2014/119676
PCT Pub. Date: Aug. 7, 2014

(65) Prior Publication Data
US 2015/0377959 A1 Dec. 31, 2015

(30) Foreign Application Priority Data

Feb. 1, 2013 (JP) ................................. 2013-018683

(51) Int. Cl.
*G01R 31/311* (2006.01)
*G01N 21/95* (2006.01)
(Continued)

(52) U.S. Cl.
CPC ......... *G01R 31/311* (2013.01); *G01N 21/9501* (2013.01); *G01R 23/16* (2013.01); *H01L 22/12* (2013.01); *G01N 2201/12* (2013.01)

(58) Field of Classification Search
CPC ...................................................... G01R 23/16
See application file for complete search history.

(56) References Cited

U.S. PATENT DOCUMENTS 5,767,688 A 6/1998 Takahashi et al.
5,905,577 A 5/1999 Wilsher et al.
(Continued)

FOREIGN PATENT DOCUMENTS

JP H1-169862 7/1989
JP H05-13522 A 1/1993
(Continued)

*Primary Examiner* — Jermele M Hollington
(74) *Attorney, Agent, or Firm* — Drinker Biddle & Reath LLP

(57) ABSTRACT

A semiconductor device inspection system includes a laser beam source, a tester, an optical sensor, a first spectrum analyzer for measuring first phase information serving as phase information of the detection signal, a reference signal generating unit for generating a reference signal of a predetermined frequency, a second spectrum analyzer for measuring second phase information serving as phase information of a reference signal, and an analysis unit for deriving phase information of the detection signal at the predetermined frequency, wherein the first spectrum analyzer measures the first phase information with respect to the reference frequency, the second spectrum analyzer measures the second phase information with respect to the reference frequency, and the frequency of the base signal of the first spectrum analyzer and the phase thereof are synchronized with the frequency of the base signal of the second spectrum analyzer and the phase thereof.

25 Claims, 2 Drawing Sheets

(51) Int. Cl.
    *G01R 23/16*     (2006.01)
    *H01L 21/66*     (2006.01)

(56)     References Cited

U.S. PATENT DOCUMENTS

| | | |
|---|---|---|
| 6,232,765 B1 | 5/2001 | Takeuchi et al. |
| 6,252,222 B1 | 6/2001 | Kasapi et al. |
| 6,976,234 B2 | 12/2005 | Kasapi |
| 7,659,981 B2 | 2/2010 | Lo et al. |
| 9,099,350 B2 * | 8/2015 | Nakamura .............. H01L 22/12 |
| 2007/0046301 A1 | 3/2007 | Kasapi |
| 2010/0039131 A1 | 2/2010 | Kasapi |
| 2012/0307249 A1 | 12/2012 | Nakamura et al. |
| 2015/0130474 A1* | 5/2015 | Nakamura .............. G01R 23/17 |
| | | 324/501 |
| 2015/0276865 A1* | 10/2015 | Nakamura ....... G01N 21/95607 |
| | | 324/754.23 |
| 2015/0309115 A1* | 10/2015 | Nakamura ......... G01R 19/0084 |
| | | 324/754.23 |
| 2015/0369755 A1* | 12/2015 | Nakamura ......... G01N 21/9501 |
| | | 356/237.5 |

FOREIGN PATENT DOCUMENTS

| | | |
|---|---|---|
| JP | H5-047883 | 2/1993 |
| JP | H05-164788 A | 6/1993 |
| JP | H06-201803 | 7/1994 |
| JP | H07-134147 A | 5/1995 |
| JP | H08-211131 A | 8/1996 |
| JP | 2001-255354 A | 9/2001 |
| JP | 2007-064975 A | 3/2007 |
| JP | 2010-271307 A | 12/2010 |
| KR | 10-1996-0035045 | 10/1996 |

\* cited by examiner

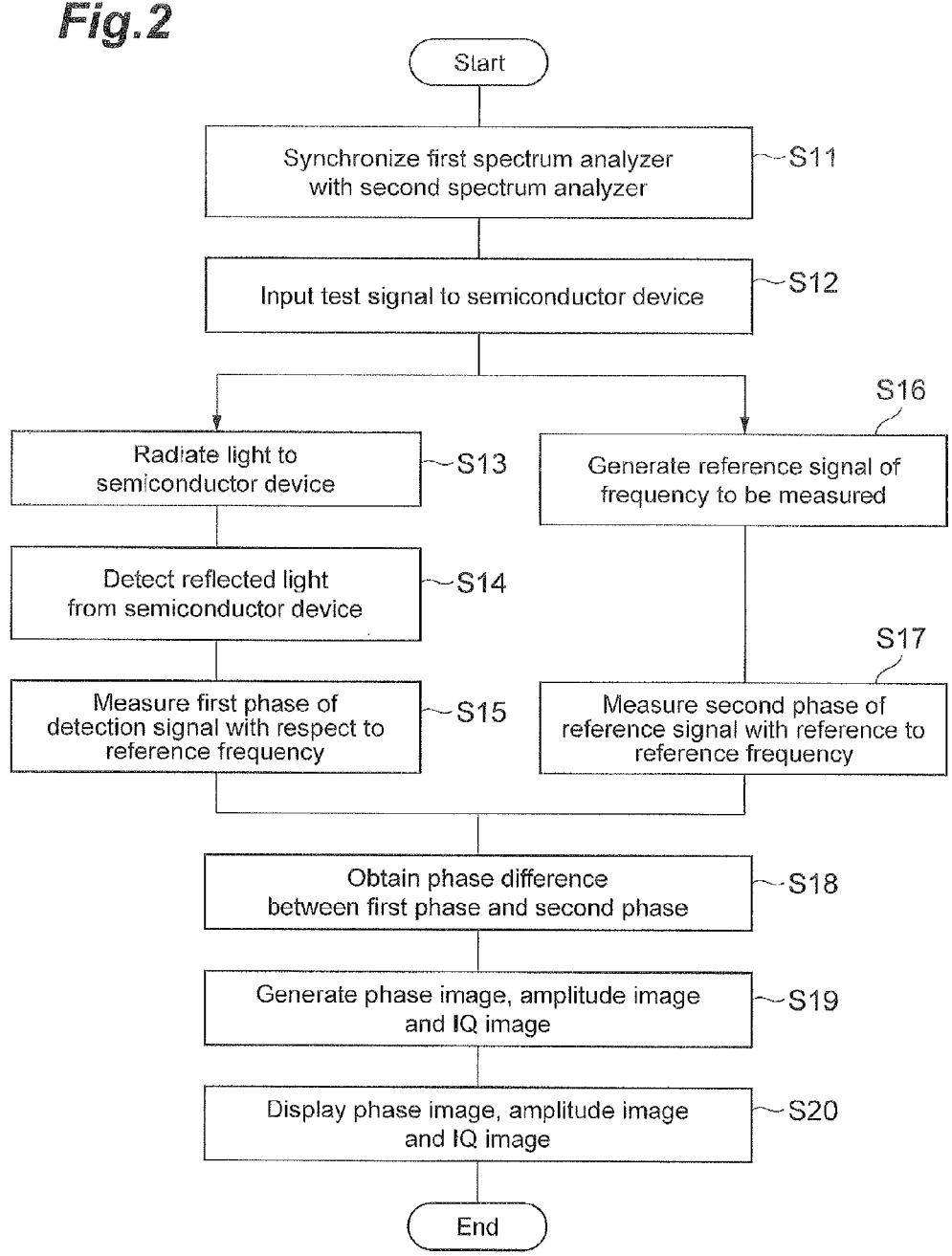

SEMICONDUCTOR DEVICE INSPECTION DEVICE AND SEMICONDUCTOR DEVICE INSPECTION METHOD

TECHNICAL FIELD

The present invention relates to a semiconductor device inspection system and a semiconductor device inspection method.

BACKGROUND ART

As a technology of inspecting an integrated circuit, optical probing technologies referred to as electro optical probing (EOP) and electro-optical frequency mapping (EOFM) are known. In such optical probing technologies, light emitted from a light source is irradiated to an integrated circuit, and the light reflected by the integrated circuit is detected by an optical sensor to acquire a detection signal. Then, in the acquired detection signal, a desired frequency is selected, and amplitude energy thereof is displayed as time progression or two-dimensional mapping is displayed. Accordingly, a position of the circuit operated at a desired frequency can be specified.

CITATION LIST

Patent Literature

[Patent Literature 1] Japanese Unexamined Patent Application, First Publication No. 2007-64975
[Patent Literature 2] Japanese Unexamined Patent Application, First Publication No. 2010-271307

SUMMARY OF INVENTION

Technical Problem

The above-mentioned optical probing technology is extremely effective technology because a portion in which a failure occurs, a cause of a failure, and so on, in a semiconductor device such as an integrated circuit can be specified.

Here, the present invention is directed to provide a semiconductor device inspection system and a semiconductor device inspection method that are capable of precisely performing inspection of a semiconductor device.

Solution to Problem

A semiconductor device inspection system according to an aspect of the present invention includes a light generating unit for generating light to be irradiated a semiconductor device serving as a device under test; a test signal application unit for applying a test signal that operates the semiconductor device to the semiconductor device; a light detection unit for detecting the light reflected by the semiconductor device and outputting a detection signal when the light is irradiated to the semiconductor device; a first spectrum analyzer, to which the detection signal is input, for measuring first phase information serving as phase information of the detection signal; a reference signal generating unit for generating a reference signal of a predetermined frequency; a second spectrum analyzer, to which the reference signal is input, for measuring second phase information serving as phase information of the reference signal; and an analysis unit for deriving phase information of the detection signal at the predetermined frequency based on the first phase information and the second phase information, wherein the first spectrum analyzer measures the first phase information with respect to a frequency of a base signal that operates the first spectrum analyzer, the second spectrum analyzer measures the second phase information with respect to a frequency of a base signal that operates the second spectrum analyzer, and the frequency and the phase of the base signal of the first spectrum analyzer are synchronized with the frequency and the phase of the base signal of the second spectrum analyzer.

In the semiconductor device inspection system, the phase information (the first phase information) of the detection signal with respect to the frequency of the base signal is measured in the first spectrum analyzer. In addition, the phase information (the second phase information) of the reference signal of the predetermined frequency with respect to the frequency of the base signal is measured in the second spectrum analyzer. Then, the phase information of the detection signal at the predetermined frequency is derived from the phase difference between the first phase information and the second phase information. Accordingly, as the predetermined frequency of the reference signal is set to the frequency to be measured, the phase information of the detection signal at the frequency to be measured can be derived. Here, the frequency of the base signal of the first spectrum analyzer and the phase thereof are synchronized with the frequency of the base signal of the second spectrum analyzer and the phase thereof. Accordingly, since the phase difference due to operations of the spectrum analyzers is prevented from overlapping, the phase difference between the first phase information and the second phase information, i.e., the phase difference between the phase information of the detection signal and the phase information of the reference signal can be precisely derived. Further, synchronization of the frequency of the base signal includes the same frequency, and in synchronization of the phase, the phase difference between the base signals is fixed to a zero state or a specified phase difference, and includes a state in which the phase difference is set to 0 through correction. As described above, according to the semiconductor device inspection system, the phase information of the detection signal at the frequency to be measured can be precisely obtained, and as a result, inspection of the semiconductor device can be precisely performed.

In the semiconductor device inspection system according to the aspect of the present invention, both of the frequency of the base signal of the first spectrum analyzer and the frequency of the base signal of the second spectrum analyzer may be the predetermined frequency. As the frequency of the base signal is set to the predetermined frequency, the amplitude (intensity) and the phase of the detection signal at the predetermined frequency, i.e., the frequency to be measured, can be simultaneously measured.

In the semiconductor device inspection system according to the aspect of the present invention, the semiconductor device inspection system may further include a synchronization unit electrically coupled to the first spectrum analyzer and the second spectrum analyzer and for synchronizing the frequency and the phase of the base signal of the first spectrum analyzer with the frequency and the phase of the base signal of the second spectrum analyzer. As the synchronization unit is provided, an overlapping prevention effect of the phase difference due to the operations of the spectrum analyzers can be more securely exhibited.

In the semiconductor device inspection system according to the aspect of the present invention, the above-mentioned predetermined frequency may be a frequency n times the frequency of the test signal, and n may be a positive integer. For example, as the reference signal generating unit is electrically coupled to the test signal application unit and the predetermined frequency is a frequency (a frequency synchronized with the frequency of the test signal) n times the frequency of the test signal, the reference signal of the predetermined frequency can be easily generated.

The semiconductor device inspection system according to the aspect of the present invention may further include a light scanning unit for receiving the light generated by the light generating unit and scanning the light to a predetermined radiation position of the semiconductor device; and an image generating unit for generating a phase image at the predetermined frequency based on the radiation position to which the light is scanned by the light scanning unit and the phase information of the detection signal at the predetermined frequency derived from the analysis unit. As the phase image at the predetermined frequency is generated based on the radiation position by the light scanning unit and the phase information of the detection signal at the predetermined frequency derived by the analysis unit, the phase state of the semiconductor device that operates at the predetermined frequency can be observed. Further, as the phase image is generated in consideration of the radiation position (for example, a position on an x-axis and a y-axis that are perpendicular to each other), the phase of the detection signal at the predetermined frequency can be observed by performing two-dimensional mapping or the like at each radiation position.

In the semiconductor device inspection system according to the aspect of the present invention, the first spectrum analyzer may measure amplitude information of the detection signal at the predetermined frequency. As the predetermined frequency of the reference signal is set to the frequency to be measured, the amplitude information of the detection signal at the frequency to be measured can be derived.

The semiconductor device inspection system according to the aspect of the present invention may further include a light scanning unit for receiving the light generated by the light generating unit and scanning the light to a predetermined radiation position of the semiconductor device; and an image generating unit for generating an amplitude image at the predetermined frequency based on the radiation position to which the light is scanned by the light scanning unit and the amplitude information of the detection signal at the predetermined frequency measured by the first spectrum analyzer. As the amplitude image at the predetermined frequency is generated based on the radiation position by the light scanning unit and the amplitude information of the detection signal at the predetermined frequency measured by the first spectrum analyzer, the amplitude state of the semiconductor device that operates at the predetermined frequency can be observed. Further, as the amplitude image is generated in consideration of the radiation position (for example, a position on an x-axis and a y-axis that are perpendicular to each other), the amplitude of the detection signal at the predetermined frequency can be observed by performing the two-dimensional mapping or the like at each radiation position.

The semiconductor device inspection system according to the aspect of the present invention may further include a light scanning unit for receiving the light generated by the light generating unit and scanning the light to a predetermined radiation position of the semiconductor device; and an image generating unit for generating an image related to an in-phase component and a quadrature component at the predetermined frequency based on the radiation position to which the light is scanned by the light scanning unit, the phase information of the detection signal at the predetermined frequency derived by the analysis unit, and the amplitude information of the detection signal at the predetermined frequency measured by the first spectrum analyzer. As the image related to the in-phase component and the quadrature component at the predetermined frequency is generated based on the radiation position by the light scanning unit, the phase information of the detection signal at the predetermined frequency derived by the analysis unit, and the amplitude information of the detection signal at the predetermined frequency measured by the first spectrum analyzer, the state of the in-phase component and the quadrature component of the semiconductor device that operates at the predetermined frequency can be observed. Further, as the image related to the in-phase component and the quadrature component in consideration of the radiation position (for example, a position on an x-axis and a y-axis that are perpendicular to each other) is generated, the in-phase component and the quadrature component of the detection signal at the predetermined frequency can be observed by performing the two-dimensional mapping or the like at each radiation position.

A semiconductor device inspection method according to an aspect of the present invention includes irradiating light to a semiconductor device serving as a device under test; applying a test signal to the semiconductor device; detecting the light reflected by the semiconductor device and outputting the detection signal when the light is irradiated to the semiconductor device; measuring first phase information serving as phase information of the detection signal with respect to a frequency of a base signal that operates a first spectrum analyzer; measuring second phase information serving as phase information of the reference signal with respect to a frequency of a base signal that operates a second spectrum analyzer; and deriving phase information of the detection signal at the predetermined frequency based on the first phase information and the second phase information, wherein a frequency and a phase of the base signal of the first spectrum analyzer are synchronized with a frequency and a phase of the base signal of the second spectrum analyzer.

In the semiconductor device inspection method according to the aspect of the present invention, both of the frequency of the base signal of the first spectrum analyzer and the frequency of the base signal of the second spectrum analyzer may be the predetermined frequency.

In the semiconductor device inspection method according to the aspect of the present invention, the predetermined frequency may be a frequency n times the frequency of the test signal, and n may be a positive integer.

The semiconductor device inspection method according to the aspect of the present invention may further include scanning the light to a predetermined radiation position of the semiconductor device; and generating a phase image at the predetermined frequency based on the radiation position to which the light is scanned in the scanning of the light, and the phase information of the detection signal at the predetermined frequency derived in the deriving of the phase information of the detection signal.

The semiconductor device inspection method according to the aspect of the present invention may further include measuring amplitude information of the detection signal at the predetermined frequency by the first spectrum analyzer.

The semiconductor device inspection method according to the aspect of the present invention may further include scanning the light to the predetermined radiation position of the semiconductor device; and generating an amplitude image at the predetermined frequency based on the radiation position to which the light is scanned in the scanning of the light, and the amplitude information of the detection signal at the predetermined frequency measured in the measuring of the amplitude information of the detection signal.

The semiconductor device inspection method according to the aspect of the present invention may further include scanning the light to the predetermined radiation position of the semiconductor device; and generating an image related to an in-phase component and a quadrature component at the predetermined frequency based on the radiation position to which the light is scanned in the scanning of the light, the phase information of the detection signal at the predetermined frequency derived in the deriving of the phase information of the detection signal, and the amplitude information of the detection signal at the predetermined frequency measured in the measuring of the amplitude information of the detection signal.

Advantageous Effects of Invention

According to an aspect of the present invention, inspection of a semiconductor device can be precisely performed.

BRIEF DESCRIPTION OF DRAWINGS

FIG. 2 is a flowchart showing a flow of a semiconductor device inspection method.

DESCRIPTION OF EMBODIMENTS

Figure 1:
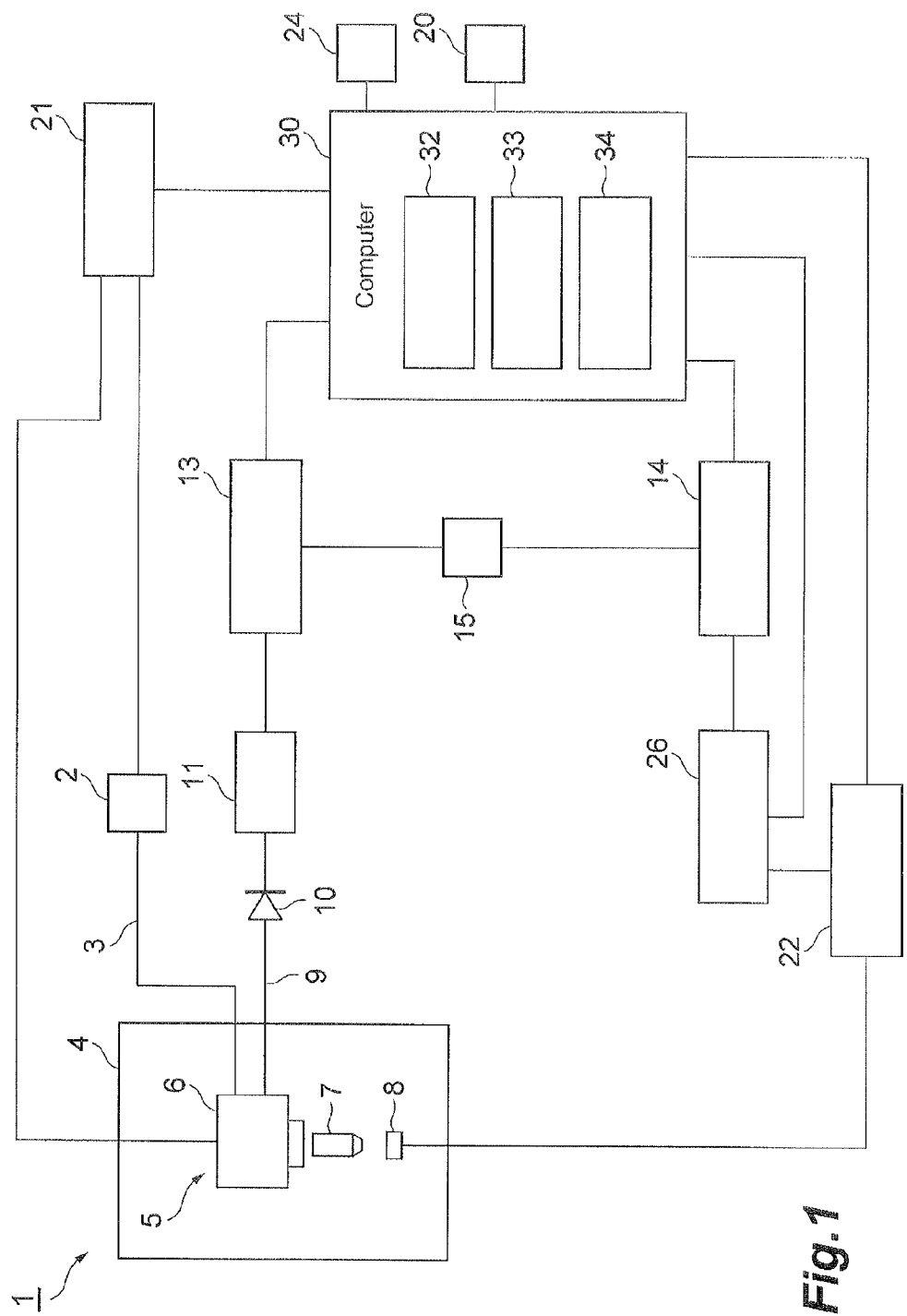
FIG. 1 is a configuration view of a semiconductor device inspection system of an embodiment of the present invention.

Hereinafter, an embodiment of the present invention will be described in detail with reference to the accompanying drawings. Further, the same or corresponding portions of the drawings are designated by the same reference numerals, and overlapping description thereof will be omitted.

As shown in FIG. 1, a semiconductor device inspection system 1 is a device for inspecting a semiconductor device 8, for example, specifying a place in which an abnormality occurs in the semiconductor device 8 serving as a device under test (DUT), and so on. As the semiconductor device 8, there are provided an integrated circuit having a PN junction such as a transistor or the like (for example, a small scale integrated (SSI) circuit, a medium scale integrated (MSI) circuit, a large scale integrated (LSI) circuit, a very large scale integrated (VLSI) circuit, an ultra large scale integrated (ULSI) circuit, and a giga scale integrated (GSI) circuit), a MOS transistor for large current/high pressure, a bipolar transistor, and so on. In addition, the semiconductor device 8 may be a semiconductor device in which modulation is applied to a substrate by heat.

The semiconductor device inspection system 1 includes a laser beam source (a light generating unit) 2. The laser beam source 2 is operated by a first power source (not shown), and generates and emits light to be irradiated to the semiconductor device 8. The laser beam source 2 is a lamp system laser beam source, a laser diode, or the like, configured to generate a laser beam, which is coherent light. The light emitted from the laser beam source 2 is optically guided to a scan optical system (a light scanning unit) 5 via a polarization preservation single mode optical fiber 3 for probe light.

The scan optical system 5 has a scan head 6 and a lens system, and for example, is constituted by an optical scanning element such as a galvanometer mirror or the like. The light guided to the scan optical system 5 is collected (condensed) onto the semiconductor device 8 by an object lens 7. Accordingly, the image of the light guided to the scan optical system 5 is formed at a predetermined radiation position of the semiconductor device 8. The radiation position of the light is two-dimensionally scanned with respect to the semiconductor device 8 by the scan optical system 5. The radiation position scanned by the scan optical system 5 is controlled by a laser scan controller 21. The laser scan controller 21 designates a radiation position as two-dimensional position information represented by a position (x position, y position) on an x-axis and a y-axis with respect to the scan optical system 5. The laser scan controller 21 inputs the radiation position represented by the x position and the y position to a computer 30. Further, the scan optical system 5, the object lens 7, and the semiconductor device 8 are disposed in a black box 4.

The light reflected by the semiconductor device 8 when the light emitted from the laser beam source 2 is irradiated to the semiconductor device 8 is returned to the scan optical system 5 by the object lens 7 and optically guided to an optical sensor (a light detection unit) 10 via an optical fiber 9 for optical feedback. The optical sensor 10 is operated by a second power source (not shown) installed separately from the first power source (not shown), and detects the reflected light to output a detection signal. The semiconductor device inspection system 1 according to the embodiment is configured to obtain a phase in a predetermined frequency (a frequency to be measured) of the detection signal. The optical sensor 10 is constituted by, for example, a photodiode, an avalanche photodiode, a photomultiplier tube, an area image sensor, or the like. The detection signal output from the optical sensor 10 is input to a spectrum analyzer 13 via an amplifier 11. The amplifier 11 amplifies the detection signal. More specifically, the amplifier 11 particularly amplifies an AC component (an RF signal) of the detection signal.

In general, the spectrum analyzer has a function of measuring a phase between an internal reference frequency source (for example, a synthesizer) and an external signal. For this reason, the spectrum analyzer (a first spectrum analyzer) 13 measures a phase (phase information) of the detection signal based on the detection signal amplified by the amplifier 11. The phase of the detection signal is first phase information. More specifically, the spectrum analyzer 13 measures the phase of the detection signal with respect to the reference frequency. Here, the reference frequency is a frequency of a base signal that operates the spectrum analyzer 13, and a frequency of a synthesizer (a synthesizer built in the spectrum analyzer 13) that becomes a time base of the spectrum analyzer 13. That is, the spectrum analyzer 13 measures a phase of an input signal (a detection signal) input to the spectrum analyzer 13 with respect to a frequency (a reference frequency) of the synthesizer built therein. The reference frequency, i.e., the frequency of the synthesizer, is set to, for example, a frequency to be measured in the detection signal. Accordingly, the spectrum analyzer 13 can simultaneously measure amplitude (amplitude information) and a phase of the detection signal at the frequency to be measured. The spectrum analyzer 13 outputs the phase of the detection signal at the frequency to be measured, and the amplitude of the detection signal at the frequency to be measured. The phase of the detection signal at the frequency to be measured and the amplitude of the detection signal at the frequency to be measured, which are output from the spectrum analyzer 13, are input to the computer 30. Further, synchronization of the spectrum analyzers is performed at a frequency (for example, 10 MHz), which is not a frequency to be measured. Accordingly, since the phase is offset at a frequency other than 10 MHz, the phase offset may be measured and calibrated.

A tester (a test signal application unit) 22 is electrically coupled to the semiconductor device 8. The tester 22 repeatedly applies a predetermined test signal (a test pattern) to the semiconductor device 8. An element such as a transistor or the like formed in the semiconductor device 8 is operated by the test signal. Since various transistors are formed in the semiconductor device 8, a plurality of operating frequencies are present according to combination of ON/OFF of the transistors. For this reason, a plurality of modulation frequencies of the reflected light from the semiconductor device 8 are also present. A reference signal generating unit 26 is electrically coupled to the tester 22.

The reference signal generating unit 26 generates a reference signal having a predetermined frequency. A frequency to measure the phase of the detection signal is set as the predetermined frequency. The reference signal generating unit 26 may be a pulse generator of the tester 22, or a pulse generator of the outside connected to the tester 22 electrically or in another way. For this reason, the reference signal generated by the reference signal generating unit 26 can be synchronized with the test signal. Further, the reference signal synchronized with the test signal includes a state in which the frequency of the reference signal is a frequency n times (n is a positive integer) the frequency of the test signal, and the phase of the reference signal and the phase of the test signal are fixed to a state in which a phase difference between is 0 or fixed to a specified phase difference, and the phase difference may be set to 0 through correction. For this reason, the reference signal generating unit 26 generates, for example, a reference signal of a frequency n times (n is a positive integer) the frequency of the test signal as the reference signal of a predetermined frequency (a frequency to be measured). Further, the reference signal generating unit 26 may vary the frequency of the reference signal by repeatedly combining the test signals applied from the tester 22. The reference signal of the frequency to be measured, which is generated by the reference signal generating unit 26, is input to a spectrum analyzer 14. Further, when the reference signal is input to the spectrum analyzer 14, since the reference signal may go around and cut into the measurement signal via the ground, the reference signal may be appropriately attenuated.

The spectrum analyzer (a second spectrum analyzer) 14 receives the reference signal and measures a phase of the reference signal (phase information). The phase of the reference signal is second phase information. More specifically, the spectrum analyzer 14 measures the phase of the reference signal with respect to the reference frequency. Here, the reference frequency is a frequency of the base signal that operates the spectrum analyzer 14, and is a frequency of a synthesizer (a synthesizer built in the spectrum analyzer 14) serving as a time base of the spectrum analyzer 14. That is, the spectrum analyzer 14 measures a phase of an input signal (the reference signal) with respect to the frequency (the reference frequency) of the built-in synthesizer and input to the spectrum analyzer 14.

Here, the reference frequency of the spectrum analyzer 13 and the phase thereof, and the reference frequency of the spectrum analyzer 14 and the phase thereof are synchronized (described in detail later). That is, the frequency and the phase of the synthesizer of the spectrum analyzer 13 are synchronized with the frequency and the phase of the synthesizer of the spectrum analyzer 14. Further, the synchronization of the phase includes a state in which a phase difference between the base signals is fixed to a zero state or a specified phase difference, and the phase difference may be set to 0 through correction. Accordingly, the reference frequency of the spectrum analyzer 14 is set to, for example, a frequency to be measured of the detection signal, like the reference frequency of the spectrum analyzer 13. As described above, since the reference signal input to the spectrum analyzer 14 is also the frequency to be measured, if the reference signal is synthesized with the synthesizer of the spectrum analyzer 14, the phase of the reference signal with respect to the reference frequency becomes 0°. However, in the embodiment, since the reference signal is not synthesized with the synthesizer of the spectrum analyzer 14, a slight phase difference occurs between the reference frequency and the reference signal. The spectrum analyzer 14 measures the slight phase difference as the phase of the reference signal with respect to the reference frequency. The spectrum analyzer 14 outputs the phase of the reference signal with respect to the reference frequency (the phase of the reference signal at the frequency to be measured). The phase of the reference signal output from the spectrum analyzer 14 and with respect to the reference frequency is input to the computer 30.

The spectrum analyzer 13 and the spectrum analyzer 14 are electrically coupled to each other via a synchronization unit 15. The synchronization unit 15 is electrically coupled to the spectrum analyzer 13 and the spectrum analyzer 14, and the reference frequency of the spectrum analyzer 13 and the phase thereof are synchronized with the reference frequency of the spectrum analyzer 14 and the phase thereof. Specifically, the synchronization unit 15 generates a time base signal of the reference frequency and inputs the time base signal to the spectrum analyzer 13 and the spectrum analyzer 14. The synthesizers of the spectrum analyzer 13 and the spectrum analyzer 14 synchronize the phases of the reference frequencies by synchronizing the time bases with the above-mentioned time base signal. Further, when the spectrum analyzer 13 and the spectrum analyzer 14 are operated using a common synthesizer, the common synthesizer has a function of the above-mentioned synchronization unit 15, and when either the spectrum analyzer 13 or the spectrum analyzer 14 operates the other spectrum analyzer using either one of the synthesizers, either one of the synthesizers has a function of the above-mentioned synchronization unit 15.

The computer 30 is, for example, a PC. The computer 30 has a control unit 32 configured to control various devices of the semiconductor device inspection system 1 such as the reference signal generating unit 26, the tester 22, the laser scan controller 21, and so on, an analysis unit 33 configured to derive the phase of the detection signal at the predetermined frequency (a frequency to be measured), and an image generating unit 34 configured to generate an image. Further, various information in response to manipulation of a user can be input to the computer 30 from an input unit 24. The input unit 24 is, for example, a keyboard or the like.

The analysis unit 33 derives the phase of the detection signal at the predetermined frequency (the frequency to be measured) based on the phase of the detection signal with respect to the reference frequency input by the spectrum analyzer 13 and the phase of the reference signal with respect to the reference frequency input by the spectrum analyzer 14. Specifically, the analysis unit 33 acquires a phase difference between the phase of the detection signal with respect to the reference frequency and the phase of the reference signal with respect to the reference frequency. The phase difference is the phase of the detection signal with respect to the reference signal, i.e., corresponds to the phase (phase information) of the detection signal at the predetermined frequency (the frequency to be measured) of the reference signal. The phase of the detection signal at the frequency to be measured is displayed on a display unit 20. In addition, the analysis unit 33 inputs the phase of the detection signal at the frequency to be measured to the image generating unit 34.

The image generating unit 34 generates a phase image at the frequency to be measured, based on a radiation position (x position, y position) of the scan optical system 5 input by the laser scan controller 21 and the phase of the detection signal at the frequency to be measured input by the analysis unit 33. As described above, since the radiation position is designated by two-dimensional position information, a phase image obtained by two-dimensionally mapping the phase of the detection signal at the frequency to be measured at each radiation position can be generated. The two-dimensionally mapped phase image is displayed on the display unit 20.

In addition, the image generating unit 34 generates an amplitude image at the frequency to be measured, based on a radiation position (x position, y position) of the scan optical system 5 input by the laser scan controller 21 and an amplitude of the detection signal at the frequency to be measured input by the spectrum analyzer 13. As described above, since the radiation position is designated by two-dimensional position information, an amplitude image obtained by two-dimensionally mapping the amplitude of the detection signal at the frequency to be measured at each radiation position can be generated. The two-dimensionally mapped amplitude image is displayed on the display unit 20.

In addition, the image generating unit 34 generates an IQ image at the frequency to be measured, based on the radiation position (x position, y position) of the scan optical system 5 input by the laser scan controller 21, the phase of the detection signal at the frequency to be measured input by the analysis unit 33, and the amplitude of the detection signal at the frequency to be measured input by the spectrum analyzer 13. "I" of the IQ image is "in-phase," and represents an in-phase component at the frequency to be measured. In addition, "Q" is "quadrature," and represents a quadrature component of the frequency to be measured. At the frequency to be measured, an image obtained by mapping the in-phase component and the quadrature component of the detection signal at each radiation position is an IQ image.

Next, a flow of an inspection method of the semiconductor device 8 by the semiconductor device inspection system 1 will be described with reference to FIG. 2.

First, the reference frequency of the spectrum analyzer 13 and the phase thereof are synchronized with the reference frequency of the spectrum analyzer 14 and the phase thereof by the synchronization unit 15 (step S11). Next, the test signal is applied (input) to the semiconductor device 8 by the tester 22 (step S12). Next, the light emitted from the laser beam source 2 is irradiated to the semiconductor device 8 via the scan optical system 5 (step S13). Then, the light reflected by the semiconductor device 8 is detected by the optical sensor 10 (step S14).

The light detected by the optical sensor 10 is output as the detection signal, and input to the spectrum analyzer 13 after being amplified by the amplifier 11. Then, the phase (first phase information) of the detection signal in the reference frequency is measured by the spectrum analyzer 13 (step S15). Further, the reference frequency is set to the frequency to be measured in the detection signal. For this reason, the amplitude (amplitude information) and the phase of detection signal at the frequency to be measured are simultaneously measured by the spectrum analyzer 13.

In addition, after processing of S12 is performed, the reference signal of the frequency synchronized with the test signal for measuring the phase of the detection signal is generated by the reference signal generating unit 26 (step S16). Next, the phase (second phase information) of the reference signal with respect to the reference frequency is measured by the spectrum analyzer 14 (step S17).

Next, a phase difference between the phase of the detection signal with respect to the reference frequency and the phase of the reference signal with respect to the reference frequency is obtained by the analysis unit 33 of the computer 30 (step S18). Then, the phase image, the amplitude image, and the IQ image are generated by the image generating unit 34 (step S19), and the generated image is displayed on the display unit 20 (step S20).

As described above, in the semiconductor device inspection system 1, phase information (first phase information) of the detection signal with respect to the reference frequency is measured in the spectrum analyzer 13. In addition, in the spectrum analyzer 14, phase information (second phase information) of the reference signal of the predetermined frequency with respect to the reference frequency is measured. Then, the phase information of the detection signal at the predetermined frequency is derived from the phase difference between the first phase information and the second phase information. Accordingly, as the predetermined frequency of the reference signal synchronized with the test signal is used as the frequency to be measured, the phase information of the detection signal at the frequency to be measured can be derived. Here, the reference frequency of the spectrum analyzer 13 and the phase thereof are synchronized with the reference frequency of the spectrum analyzer 14 and the phase thereof. Accordingly, since the phase difference due to the operations of the spectrum analyzers 13 and 14 is prevented from overlapping, the phase difference between the first phase information and the second phase information, i.e., the phase difference between the phase information of the detection signal and the phase information of the reference signal can be precisely derived. As described above, according to the semiconductor device inspection system 1, the phase information of the detection signal at the frequency to be measured can be precisely obtained, and as a result, inspection of the semiconductor device can be precisely performed.

In addition, as both of the reference frequency of the spectrum analyzer 13 and the reference frequency of the spectrum analyzer 14 are set to the frequency to be measured in the above-mentioned detection signal, the amplitude (intensity) and the phase of the detection signal at the frequency to be measured can be simultaneously measured.

In addition, since the synchronization unit 15 electrically coupled to the spectrum analyzer 13 and the spectrum analyzer 14 and configured to synchronize the reference frequency of the spectrum analyzer 13 and the phase thereof with the reference frequency of the spectrum analyzer 14 and the phase thereof is further provided, an overlapping prevention effect of the phase difference due to the operations of the spectrum analyzers 13 and 14 can be more securely exhibited.

In addition, the frequency of the reference signal generated by the reference signal generating unit 26 is a frequency n times (n is a positive integer) the frequency of the test signal. In the configuration in which the reference signal generating unit 26 is electrically coupled to the tester 22, as the frequency of the reference signal is the frequency n times the frequency of the test signal, the reference signal synchronized with the test signal can be easily generated based on the test signal.

In addition, based on the radiation position to which the light is scanned by the scan optical system 5 and the phase information of the detection signal at the predetermined frequency derived by the analysis unit 33, as the image generating unit 34 generates the phase image at the predetermined frequency, the phase state of the semiconductor device 8 that operates at the predetermined frequency can be observed. Further, as the phase image is generated in consideration of the radiation position (for example, a position on an x-axis and a y-axis, which are perpendicular to each other), the phase of the detection signal at the predetermined frequency can be observed by performing the two-dimensional mapping or the like at each radiation position.

In addition, as the spectrum analyzer 13 measures the amplitude of the detection signal at the predetermined frequency, the amplitude information of the detection signal at the frequency to be measured can be derived.

In addition, based on the radiation position to which the light is scanned by the scan optical system 5 and the amplitude information of the detection signal at the predetermined frequency measured by the spectrum analyzer 13, as the image generating unit 34 generates the amplitude image at the predetermined frequency, the amplitude state of the semiconductor device 8 that operates at a predetermined frequency can be observed. Further, as the amplitude image is generated in consideration of the radiation position (for example, a position on an x-axis and a y-axis, which are perpendicular to each other), the amplitude of the detection signal at the predetermined frequency can be observed by performing the two-dimensional mapping or the like at each radiation position.

In addition, based on the radiation position to which the light is scanned by the scan optical system 5, the phase information of the detection signal at the predetermined frequency derived from the analysis unit 33, and the amplitude information of the detection signal at the predetermined frequency measured by the spectrum analyzer 13, as the image generating unit 34 generates the IQ image at the predetermined frequency, the state of the in-phase component and the quadrature component of the semiconductor device that operates at the predetermined frequency can be observed. Further, as the images related to the in-phase component and the quadrature component are generated in consideration of the radiation position (for example, a position on an x-axis and a y-axis, which are perpendicular to each other), the in-phase component and the quadrature component of the detection signal at the predetermined frequency can be observed by performing the two-dimensional mapping or the like at each radiation position.

INDUSTRIAL APPLICABILITY

While an embodiment of the present invention has been described above, the present invention is not limited to the above-mentioned embodiment. For example, the light generating unit configured to generate the light irradiated to the semiconductor device 8 is not limited to the laser beam source 2, but another light source such as a super luminescent diode (SLD), an amplified spontaneous emission (ASE), a light emitting diode (LED), or the like, configured to generate incoherent light, may be provided. In addition, instead of an electrical signal, heat may be applied to the semiconductor device 8.

REFERENCE SIGNS LIST

1 . . . semiconductor device inspection system, 2 . . . laser beam source, 5 . . . scan optical system, 8 . . . semiconductor device, 10 . . . optical sensor, 13, 14 . . . spectrum analyzer, 15 . . . synchronization unit, 21 . . . laser scan controller, 22 . . . tester, 26 . . . reference signal generating unit, 30 . . . computer, 33 . . . analysis unit, 33 . . . image generating unit

The invention claimed is:

1. A system for inspecting a semiconductor device serving as a device under test, the system comprising:
    a light source configured to generate light to be irradiated the semiconductor device;
    a tester configured to apply a test signal to the semiconductor device;
    a light detector configured to detect the light reflected by the semiconductor device and output a detection signal;
    a first spectrum analyzer, to which the detection signal is input, configured to measure first phase information serving as phase information of the detection signal;
    a reference signal generating unit electrically coupled to the tester and configured to generate a reference signal of a predetermined frequency;
    a second spectrum analyzer, to which the reference signal is input, configured to measure second phase information serving as phase information of the reference signal; and
    an analysis unit electrically coupled to the first spectrum analyzer and the second spectrum analyzer and configured to derive phase information of the detection signal at the predetermined frequency based on the first phase information and the second phase information,
    wherein the first spectrum analyzer measures the first phase information with respect to a frequency of a base signal that operates the first spectrum analyzer,
    the second spectrum analyzer measures the second phase information with respect to a frequency of a base signal that operates the second spectrum analyzer, and
    the frequency and the phase of the base signal of the first spectrum analyzer are synchronized with the frequency and the phase of the base signal of the second spectrum analyzer.

2. The system according to claim 1, wherein both of the frequency of the base signal of the first spectrum analyzer and the frequency of the base signal of the second spectrum analyzer are the predetermined frequency.

3. The system according to claim 1, further comprising a synchronization unit electrically coupled to the first spectrum analyzer and the second spectrum analyzer and configured to synchronize the frequency and the phase of the base signal of the first spectrum analyzer with the frequency and the phase of the base signal of the second spectrum analyzer.

4. The system according to claim 1, wherein the predetermined frequency is a frequency n times the frequency of the test signal, and
    n is a positive integer.

5. The system according to claim 1, further comprising:
a light scanner configured to receive the light generated by the light source and scan the light to a predetermined radiation position of the semiconductor device; and
an image generating unit configured to generate a phase image at the predetermined frequency based on the radiation position to which the light is scanned by the light scanner and the phase information of the detection signal at the predetermined frequency derived from the analysis unit.

6. The system according to claim 1, wherein the first spectrum analyzer measures amplitude information of the detection signal at the predetermined frequency.

7. The system according to claim 6, further comprising:
a light scanner configured to receive the light generated by the light source and scan the light to a predetermined radiation position of the semiconductor device; and
an image generating unit configured to generate an amplitude image at the predetermined frequency based on the radiation position to which the light is scanned by the light scanner and the amplitude information of the detection signal at the predetermined frequency measured by the first spectrum analyzer.

8. The system according to claim 6, further comprising:
a light scanner configured to receive the light generated by the light source and scan the light to a predetermined radiation position of the semiconductor device; and
an image generating unit configured to generate an image related to an in-phase component and a quadrature component at the predetermined frequency based on the radiation position to which the light is scanned by the light scanner, the phase information of the detection signal at the predetermined frequency derived by the analysis unit, and the amplitude information of the detection signal at the predetermined frequency measured by the first spectrum analyzer.

9. A method for inspecting a semiconductor device serving as a device under test, the method comprising:
irradiating light to the semiconductor device;
applying a test signal to the semiconductor device;
detecting the light reflected by the semiconductor device and outputting the detection signal;
measuring first phase information serving as phase information of the detection signal with respect to a frequency of a base signal that operates a first spectrum analyzer;
generating a reference signal of a predetermined frequency;
measuring second phase information serving as phase information of the reference signal with respect to a frequency of a base signal that operates a second spectrum analyzer; and
deriving phase information of the detection signal at the predetermined frequency based on the first phase information and the second phase information,
wherein a frequency and a phase of the base signal of the first spectrum analyzer are synchronized with a frequency and a phase of the base signal of the second spectrum analyzer.

10. The method according to claim 9, wherein both of the frequency of the base signal of the first spectrum analyzer and the frequency of the base signal of the second spectrum analyzer are the predetermined frequency.

11. The method according to claim 9, wherein the predetermined frequency is a frequency n times the frequency of the test signal, and
n is a positive integer.

12. The method according to claim 9, further comprising:
scanning the light to a predetermined radiation position of the semiconductor device; and
generating a phase image at the predetermined frequency based on the radiation position to which the light is scanned in the scanning of the light, and the phase information of the detection signal at the predetermined frequency derived in the deriving of the phase information of the detection signal.

13. The method according to claim 9, further comprising measuring amplitude information of the detection signal at the predetermined frequency by the first spectrum analyzer.

14. The method according to claim 13, further comprising:
scanning the light to the predetermined radiation position of the semiconductor device; and
generating an amplitude image at the predetermined frequency based on the radiation position to which the light is scanned in the scanning of the light, and the amplitude information of the detection signal at the predetermined frequency measured in the measuring of the amplitude information of the detection signal.

15. The method according to claim 13, further comprising:
scanning the light to the predetermined radiation position of the semiconductor device; and
generating an image related to an in-phase component and a quadrature component at the predetermined frequency based on the radiation position to which the light is scanned in the scanning of the light, the phase information of the detection signal at the predetermined frequency derived in the deriving of the phase information of the detection signal, and the amplitude information of the detection signal at the predetermined frequency measured in the measuring of the amplitude information of the detection signal.

16. The system according to claim 1, wherein the frequency of the base signal of the first spectrum analyzer and the frequency of the base signal of the second spectrum analyzer are the same frequency.

17. The system according to claim 1, wherein the phase difference between the phase of the base signal of the first spectrum analyzer and the phase of the base signal of the second spectrum analyzer are zero.

18. The system according to claim 1, wherein the phase difference between the phase of the base signal of the first spectrum analyzer and the phase of the base signal of the second spectrum analyzer are fixed to a specified phase difference.

19. The system according to claim 1, further comprising an amplifier amplifies an AC component of the detection signal.

20. The system according to claim 1, wherein the light source is a beam source configured to generate coherent light.

21. The system according to claim 1, wherein the light source is a beam source configured to generate incoherent light.

22. The method according to claim 9, wherein the frequency of the base signal of the first spectrum analyzer and the frequency of the base signal of the second spectrum analyzer are the same frequency.

23. The method according to claim 9, wherein the phase difference between the phase of the base signal of the first spectrum analyzer and the phase of the base signal of the second spectrum analyzer are zero.

24. The method according to claim 9, wherein the phase difference between the phase of the base signal of the first spectrum analyzer and the phase of the base signal of the second spectrum analyzer are fixed to a specified phase difference.

25. The system according to claim 1, wherein the first spectrum analyzer and the second spectrum analyzer are comprised of a spectrum analyzer.

* * * * *